US010307137B2

(12) United States Patent
Nakazawa et al.

(10) Patent No.: US 10,307,137 B2
(45) Date of Patent: Jun. 4, 2019

(54) ULTRASONIC DEVICE AS WELL AS PROBE AND ELECTRONIC APPARATUS

(71) Applicant: SEIKO EPSON CORPORATION, Tokyo (JP)

(72) Inventors: Yusuke Nakazawa, Nagano (JP); Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 984 days.

(21) Appl. No.: 14/808,334

(22) Filed: Jul. 24, 2015

(65) Prior Publication Data

US 2016/0030004 A1 Feb. 4, 2016

(30) Foreign Application Priority Data

Jul. 31, 2014 (JP) ................. 2014-156707

(51) Int. Cl.
| | |
|---|---|
| *H01L 41/09* | (2006.01) |
| *A61B 8/00* | (2006.01) |
| *A61B 8/08* | (2006.01) |
| *B06B 1/06* | (2006.01) |
| *G01N 29/24* | (2006.01) |
| *G01N 29/26* | (2006.01) |
| *H01L 27/20* | (2006.01) |

(52) U.S. Cl.
CPC .......... *A61B 8/4494* (2013.01); *A61B 8/4427* (2013.01); *A61B 8/4444* (2013.01); *A61B 8/4483* (2013.01); *A61B 8/4488* (2013.01); *A61B 8/462* (2013.01); *A61B 8/5215* (2013.01); *B06B 1/067* (2013.01); *B06B 1/0629* (2013.01); *G01N 29/2437* (2013.01); *G01N 29/262* (2013.01); *H01L 27/20* (2013.01); *H01L 41/0973* (2013.01)

(58) Field of Classification Search
CPC ... A61B 8/4494; A61B 8/4427; A61B 8/4444; A61B 8/4483; A61B 8/4488; A61B 8/462; B06B 1/067; B06B 1/0629; H01L 41/0973
See application file for complete search history.

(56) References Cited

U.S. PATENT DOCUMENTS

2008/0200811 A1   8/2008 Wakabayashi et al.
2017/0055949 A1*  3/2017 Matsuda ............. A61B 8/4488

FOREIGN PATENT DOCUMENTS

| JP | 2004-105257 A | 4/2004 |
|----|---------------|--------|
| JP | 2008-110060 A | 5/2008 |
| JP | 2012-117825 A | 6/2012 |

\* cited by examiner

*Primary Examiner* — J. San Martin

(57) ABSTRACT

An ultrasonic device includes a first element row in which ultrasonic transducer elements are arranged at line-symmetrical positions along a first straight line, where a second straight line orthogonal to the first straight line is the axis of symmetry, and are connected to a first interconnect, and a second element row in which ultrasonic transducer elements are arranged at line-symmetrical positions adjacent to the first element row, where the second straight line is the axis of symmetry, and are connected to a second interconnect. When the distance between a k-th element included in the first element row and a k-th element included in the second element row is represented by $D_k$, a relationship $D_k < D_{k+1}$ is satisfied with respect to at least one value of "k".

15 Claims, 11 Drawing Sheets

US 10,307,137 B2

ULTRASONIC DEVICE AS WELL AS PROBE AND ELECTRONIC APPARATUS

BACKGROUND

1. Technical Field

The present invention relates to an ultrasonic device as well as a probe, an electronic apparatus, an ultrasonic imaging apparatus, and the like using the same.

2. Related Art

As disclosed in JP-A-2008-110060, thin-film ultrasonic transducer elements such as, for example, cMUTs (capacitive ultrasonic transducer elements) are commonly known. In JP-A-2008-110060, a cMUT is formed on a flexible sheet. Accordingly, when compared with the case where a cMUT is formed on a substrate having high stiffness, propagation of vibration is attenuated. Thus, crosstalk is suppressed, and therefore an improvement in axial resolution can be expected.

When a plurality of vibration films vibrate simultaneously, the vibration of each vibration film propagates to an adjacent vibration film through, for example, an acoustic matching layer. In this manner, so-called crosstalk occurs, and each vibration film is subjected to reverberant vibration of an adjacent vibration film. The reverberant vibration affects image formation and, for example, may add a pseudo image to an original image.

SUMMARY

According to at least one aspect of the invention, it is possible to provide an ultrasonic device that suppresses reverberant vibration.

(1) An aspect of the invention is directed to an ultrasonic device including a first interconnect and a second interconnect that are connected to a first terminal, a first element row in which "n" ultrasonic transducer elements, "n" being an integer of 4 or more, are arranged at line-symmetrical positions along a first straight line, where a second straight line orthogonal to the first straight line is an axis of symmetry, and are connected to the first interconnect, and a second element row in which "n" ultrasonic transducer elements are arranged at line-symmetrical positions adjacent to the first element row, where the second straight line is the axis of symmetry, and are connected to the second interconnect, wherein when a distance between an element included in the first element row, the element being the k-th element in increasing order of distance from the second straight line, "k" being an integer between 1 and n/2−1 inclusive, and an element included in the second element row, the element being the k-th element in increasing order of distance from the second straight line, is represented by $D_k$, a relationship $D_k < D_{k+1}$ is satisfied with respect to at least one value of "k".

The inventor of the invention newly found a certain fact. According to that fact, it was found that in the ultrasonic device, the nearer the second straight line serving as the axis of symmetry of an element array region when viewed from above, the shorter the cycle of reverberant vibration. The same driving signal is supplied to the ultrasonic transducer elements of the first element row and the second element row from the first interconnect and the second interconnect. The ultrasonic transducer elements vibrate in response to the reception of the driving signal. For example, vibration of the ultrasonic transducer elements of the second element row reaches the ultrasonic transducer elements of the first element row in accordance with the distance $D_k < D_{k+1}$. Thus, synchronization of vibration is secured between ultrasonic transducer elements corresponding to each other with respect to the distance from the second straight line. For example, vibration propagating from the second element row to the first element row can serve to reduce residual vibration in the first element row.

(2) In the ultrasonic device, it is preferable that when a distance between two elements included in the first element row, the elements respectively being the j-th element and the (j+1)-th element in increasing order of distance from the second straight line, "j" being an integer between 1 and n/2−1 inclusive, is represented by $S1_j$, and a distance between two elements included in the second element row, the elements respectively being the j-th element and the (j+1)-th element in increasing order of distance from the second straight line, is represented by $S2_j$, relationships $S1_j \leq S1_{j+1}$ and $S2_j \leq S2_{j+1}$ are satisfied. The ultrasonic transducer elements belonging to the same element row are driven by the same driving signal. Since the relationship $S1_j \leq S1_{j+1}$ and the relationship $S2_j \leq S2_{j+1}$ are established within the same element row, vibration propagating between the j-th ultrasonic transducer elements and between the (j+1)-th ultrasonic transducer elements according to the distances from the second straight line can be synchronized with vibration of the destinations of propagation. Thus, the propagation contributes to a reduction of residual vibration.

(3) It is preferable that the ultrasonic transducer elements included in the second element row are arranged along a straight line that is parallel to the first straight line, and the distances $S1_j$, $S1_{j+1}$, $S2_j$, and $S2_{j+1}$ satisfy relationships $S1_j < S2_j$ and $S1_{j+1} < S2_{j+1}$. The arrangement in the second element row extends parallel to the arrangement in the first element row. Accordingly, the distance between the element rows along the second straight line can be reduced as far as possible, that is, minimized. Thus, the ultrasonic transducer elements can be efficiently arranged.

(4) It is preferable that the distance $D_k$ satisfies the relationship $D_k < D_{k+1}$ with respect to every value of "k". Synchronization of vibration is secured between the ultrasonic transducer elements. Residual vibration can thus be reliably reduced.

(5) Another aspect of the invention is directed to an ultrasonic device including a first interconnect and a second interconnect, a transmitting unit that transmits a driving signal to the first interconnect and the second interconnect at the same timing, a first element row in which "n" ultrasonic transducer elements, "n" being an integer of 4 or more, are arranged at line-symmetrical positions along a first straight line, where a second straight line orthogonal to the first straight line is an axis of symmetry, and are connected to the first interconnect, and a second element row in which "n" ultrasonic transducer elements are arranged at line-symmetrical positions adjacent to the first element row, where the second straight line is the axis of symmetry, and are connected to the second interconnect, wherein when a distance between an element included in the first element row, the element being the k-th element in increasing order of distance from the second straight line, "k" being an integer between 1 and n/2−1 inclusive, and an element included in the second element row, the element being the k-th element in increasing order of distance from the second straight line, is represented by $D_k$, a relationship $D_k < D_{k+1}$ is satisfied with respect to at least one value of "k".

In the ultrasonic device, it was found that the nearer the second straight line serving as the axis of symmetry of the element array region when viewed from above, the shorter the cycle of reverberant vibration. The same driving signal is supplied to the ultrasonic transducer elements of the first element row and the second element row from the first interconnect and the second interconnect. The ultrasonic transducer elements vibrate in response to the reception of the driving signal. For example, vibration of the ultrasonic transducer elements in the second element row reaches the ultrasonic transducer elements in the first element row in accordance with the distance $D_k<D_{k+1}$. Thus, synchronization of vibration is secured between ultrasonic transducer elements corresponding to each other with respect to the distance from the second straight line. For example, vibration propagating from the second element row to the first element row can serve to reduce residual vibration in the first element row.

(6) The ultrasonic transducer elements may each include a vibration film provided on a base and a driving element provided on the vibration film. With this configuration, a thin-film membrane vibration element can be established in the ultrasonic device.

(7) The driving element may also include a piezoelectric body and two electrodes provided on the piezoelectric body. A so-called transformer type ultrasonic transducer element can be established.

(8) The ultrasonic device may further include an acoustic matching layer that covers the first element row and the second element row. Vibration of the ultrasonic transducer elements propagates through the acoustic matching layer. Thus, synchronization of vibration is secured between ultrasonic transducer elements corresponding to each other with respect to the distance from the second straight line. For example, vibration propagating from the second element row to the first element row can serve to reduce residual vibration in the first element row.

(9) It is preferable that an area of each of the vibration films of the ultrasonic transducer elements included in the first element row is larger than an area of each of the vibration films of the ultrasonic transducer elements included in the second element row. During formation of an ultrasonic beam, vibration of the ultrasonic transducer elements included in the second element row is not transmitted to the outside from the acoustic matching layer and mainly helps to reduce reverberant vibration. Vibration control can thus be simplified.

(10) The ultrasonic device may also include a third interconnect connected to the first terminal, and a third element row in which "n" ultrasonic transducer elements are arranged at line-symmetrical positions adjacent to the first element row, where the second straight line is the axis of symmetry, and are connected to the third interconnect. At this time, it is preferable that when a distance between an element included in the first element row, the element being the k-th element in increasing order of distance from the second straight line, "k" being an integer between 1 and n/2−1 inclusive, and an element included in the third element row, the element being the k-th element in increasing order of distance from the second straight line, is represented by $D2_k$, a relationship $D2_k<D2_{k+1}$ is satisfied with respect to the at least one value of "k". A single channel may also be formed by three element rows in this manner.

(11) In the ultrasonic device, the ultrasonic transducer elements included in the second element row may be arranged along two line-symmetrical straight lines, where the second straight line is an axis of symmetry. At this time, it is preferable that a distance L1$i$ from the second straight line to an element included in the first element row, the element being the i-th element in increasing order of distance from the second straight line, "i" being an integer between 1 and n/2 inclusive, is equal to a distance L2$i$ from the second straight line to an element included in the second element row, the element being the i-th element in increasing order of distance from the second straight line. With this configuration, the arrangements in odd rows are disposed parallel to one another, and the arrangements in even rows are disposed parallel to one another.

(12) The ultrasonic device can be used in a state in which it is incorporated into a probe. At this time, it is sufficient if the probe includes the ultrasonic device and a housing that supports the ultrasonic device.

(13) The ultrasonic device can be used in a state in which it is incorporated into an electronic apparatus. At this time, it is sufficient if the electronic apparatus includes the ultrasonic device and a processor that is connected to the ultrasonic device and that processes an output from the ultrasonic device.

(14) The ultrasonic device can be used in a state in which it is incorporated into an ultrasonic imaging apparatus. At this time, it is sufficient if the ultrasonic imaging apparatus includes the ultrasonic device and a display device that displays an image generated based on an output from the ultrasonic device.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
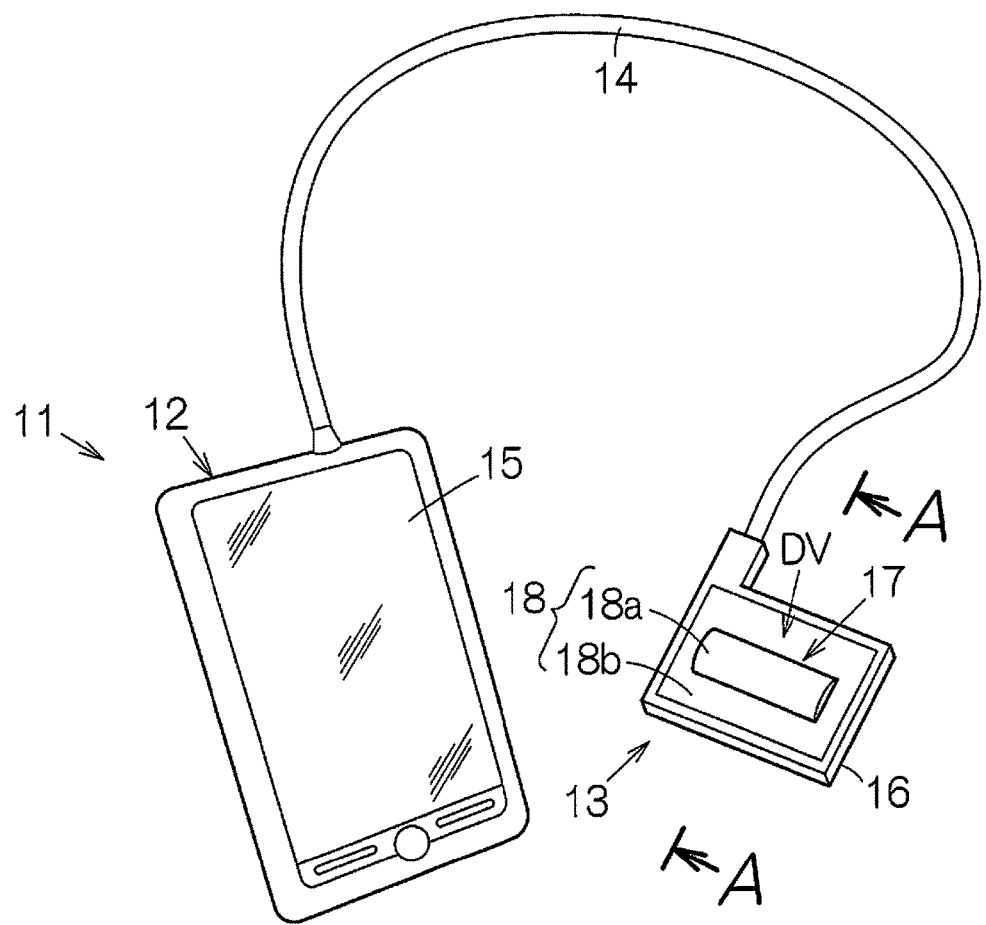
FIG. 1 is an external view schematically showing a specific example, that is, an ultrasonic diagnostic apparatus, of an electronic apparatus according to an embodiment.

FIG. 1 schematically shows the configuration of a specific example, that is, an ultrasonic diagnostic apparatus (ultrasonic imaging apparatus) 11, of an electronic apparatus according to an embodiment of the invention. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

The ultrasonic probe 13 has a housing 16. An ultrasonic device unit DV is fitted in the housing 16. The ultrasonic device unit DV includes an ultrasonic device 17. The ultrasonic device 17 includes an acoustic lens 18. A partial cylindrical surface 18a is formed on an outer surface of the acoustic lens 18. The partial cylindrical surface 18a is surrounded by a flat plate portion 18b. The entire outer perimeter of the flat plate portion 18b is continuously joined to the housing 16. Thus, the flat plate portion 18b functions as a portion of the housing. The acoustic lens 18 may be formed of, for example, a silicone resin. The acoustic lens 18 has an acoustic impedance that is similar to the acoustic impedance of a living body. The ultrasonic device 17 outputs ultrasonic waves from its surface and receives reflected waves of the ultrasonic waves.

(2) Structure of Ultrasonic Device According to First Embodiment

Figure 2:
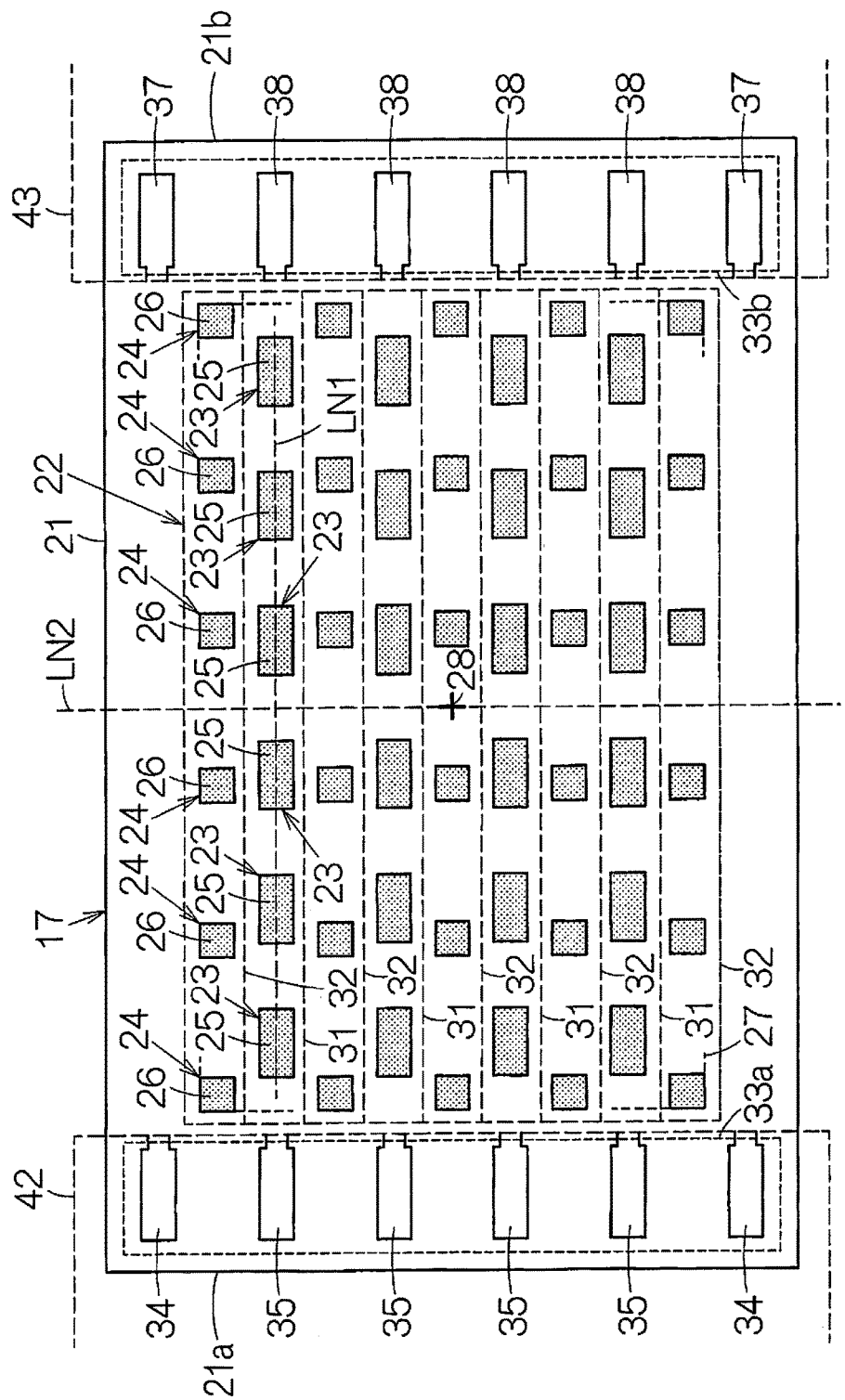
FIG. 2 is an enlarged plan view of an ultrasonic device according to a first embodiment.

FIG. 2 schematically shows a plan view of the ultrasonic device 17 according to the first embodiment. The ultrasonic device 17 includes a base 21. An element array 22 is formed on a surface (first surface) of the base 21. The element array 22 is constituted by an arrangement of "n" ("n" is an integer of 4 or more) first thin-film ultrasonic transducer elements (hereinafter referred to as "first elements") 23 and "n" second thin-film ultrasonic transducer elements (hereinafter referred to as "second elements") 24 that are arranged in an array. The first elements 23 are arranged along a first straight line LN1 at line-symmetrical positions, where a second straight line LN2 that is orthogonal to the first straight line LN1 is the axis of symmetry. Similarly, the second elements 24 are arranged along a straight line that is parallel to the first straight line LN1 at line-symmetrical positions, where the second straight line LN2 is the axis of symmetry.

The first elements 23 and the second elements 24 each include a vibration film 25 or 26. FIG. 2 shows the outlines of the vibration films 25 and 26 when viewed from above in a direction orthogonal to the film surface of the vibration films 25 and 26 (when viewed from above in a thickness direction of the substrate). The element array 22 defines an element array region 27. The outline of the element array region 27 is formed by a minimum-area quadrilateral circumscribing the vibration films 26 that are located at the outermost perimeter. When viewed from above, a centroid 28 of the outline lies on the second straight line LN2. The ultrasonic device 17 is configured as a single ultrasonic transducer element chip (substrate).

The first elements 23 are lined up in a row direction. It is sufficient if the first elements 23 are arranged in a single straight line. Each row of first elements 23 forms a driving row 31. As will be described later, ultrasonic waves emitted from the driving rows 31 are used to form an image. The driving rows 31 form first element rows of the present embodiment.

Similarly, the second elements 24 are lined up in the row direction. It is sufficient if the second elements 24 are arranged in a single straight line. Each row of second elements 24 forms a reverberation suppression row 32. As will be described later, vibration of the second elements 24 is used in cancelling out the reverberant vibration of the first elements 23 when the first elements 23 vibrate. At least one reverberation suppression row 32 is combined with a driving row 31. Here, the driving rows 31 and the reverberation suppression rows 32 are arranged alternately in a column direction. The reverberation suppression rows 32 form second element rows of the present embodiment.

The outline of the base 21 has a first side 21a and a second side 21b that are defined by a pair of mutually parallel straight lines and that oppose each other. A first terminal array 33a in a single line is disposed between the first side 21a and the outline of the element array 22. A second terminal array 33b in a single line is disposed between the second side 21b and the outline of the element array 22. The first terminal array 33a can form a single line parallel to the first side 21a. The second terminal array 33b can form a single line parallel to the second side 21b.

The first terminal array 33a includes a pair of top electrode terminals 34 and bottom electrode terminals 35. The top electrode terminals 34 are arranged at opposite ends of the first terminal array 33a. The first elements 23 belonging to all the driving rows 31 and the second elements 24 belonging to all the reverberation suppression rows 32 are connected commonly to the top electrode terminals 34. The bottom electrode terminals 35 are arranged between the top electrode terminals 34. The first elements 23 of each driving row 31 and the second elements 24 of each reverberation suppression row 32 are connected to a corresponding bottom electrode terminal 35.

Similarly, the second terminal array 33b includes a pair of top electrode terminals 37 and bottom electrode terminals 38. The top electrode terminals 37 are arranged at opposite ends of the second terminal array 33b. The first elements 23 belonging to all the driving rows 31 and the second elements 24 belonging to all the reverberation suppression rows 32 are connected commonly to the top electrode terminals 37. The bottom electrode terminals 38 are arranged between the top electrode terminals 37. The first elements 23 of each driving row 31 and the second elements 24 of each reverberation suppression row 32 are connected to a corresponding bottom electrode terminal 38.

A first flexible printed wiring board (hereinafter referred to as "first wiring board") 42 is connected to the base 21. The first wiring board 42 covers the first terminal array 33a. Electrically conductive lines, namely, first signal lines are formed at one end of the first wiring board 42, individually corresponding to the top electrode terminals 34 and the bottom electrode terminals 35. The first signal lines are individually opposed to the top electrode terminals 34 and the bottom electrode terminals 35 and individually joined thereto. Similarly, a second flexible printed wiring board (hereinafter referred to as "second wiring board") 43 covers the base 21. The second wiring board 43 covers the second terminal array 33b. Electrically conductive lines, namely, second signal lines are formed at one end of the second wiring board 43, individually corresponding to the top electrode terminals 37 and the bottom electrode terminals 38. The second signal lines are individually opposed to the top electrode terminals 37 and the bottom electrode terminals 38 and individually joined thereto.

Figure 3:
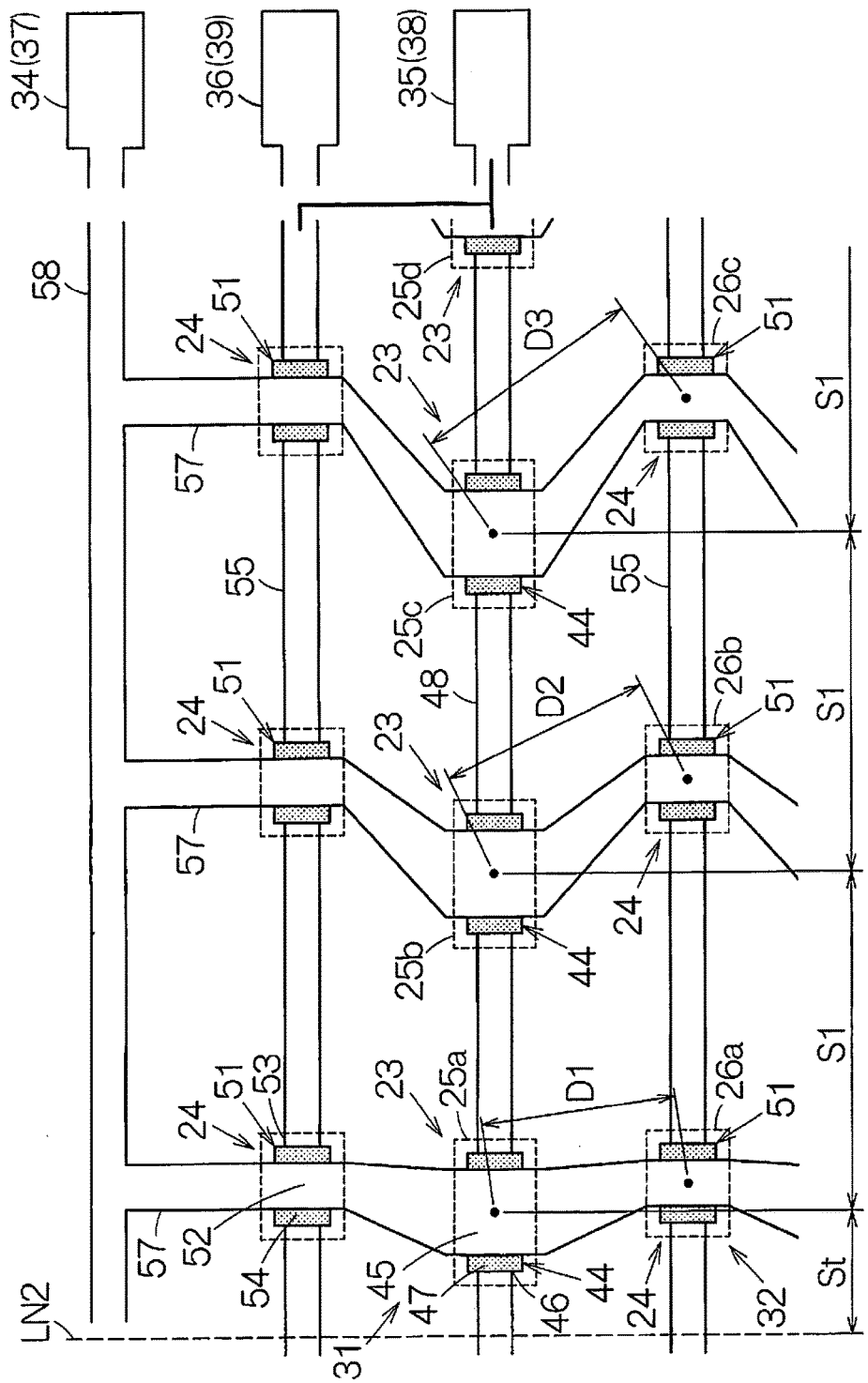
FIG. 3 is a partial enlarged plan view of the ultrasonic device.

As shown in FIG. 3, a piezoelectric element 44 is formed on the vibration film 25 of each first element 23. The piezoelectric element 44 is constituted by a top electrode 45, a bottom electrode 46, and a piezoelectric film 47. In each first element 23, the piezoelectric film 47 is sandwiched between the top electrode 45 and the bottom electrode 46. The bottom electrode 46, the piezoelectric film 47, and the top electrode 45 are laid one on top of another in that order.

On the surface of the base 21, one first electric conductor (first interconnect) 48 is formed for each driving row 31. The first electric conductor 48 extends along a straight line in the row direction of the arrangement. Each first electric conductor 48 is connected commonly to the piezoelectric films 47 of the first elements 23 belonging to a single corresponding driving row 31. The first electric conductor 48 forms the bottom electrodes 46 for the individual first elements 23. The two ends of the first electric conductor 48 are connected to the corresponding bottom electrode terminals 35 and 38, respectively. For example, a laminated film of titanium (Ti), iridium (Ir), platinum (Pt), and titanium (Ti) can be used for the first electric conductors 48. However, other electrically conductive materials may also be used for the first electric conductors 48.

A piezoelectric element 51 is formed on the vibration film 26 of each second element 24. The piezoelectric element 51 is constituted by a top electrode 52, a bottom electrode 53, and a piezoelectric film 54. In each second element 24, the piezoelectric film 54 is sandwiched between the top electrode 52 and the bottom electrode 53. The bottom electrode 53, the piezoelectric film 54, and the top electrode 52 are laid one on top of another in that order. Here, the size of the vibration films 25 of the respective first elements 23 is larger than the size of the vibration films 26 of the respective second elements 24.

On the surface of the base 21, one second electric conductor (second interconnect) 55 is formed for each reverberation suppression row 32. The second electric conductor 55 extends along a straight line in the row direction of the arrangement. Each second electric conductor 55 is connected commonly to the piezoelectric films 54 of the second elements 24 belonging to a single corresponding reverberation suppression row 32. The second electric conductor 55 forms the bottom electrodes 53 for the individual second elements 24. The two ends of the second electric conductor 55 are connected to the corresponding bottom electrode terminals 36 and 39, respectively. For example, a laminated film of titanium (Ti), iridium (Ir), platinum (Pt), and titanium (Ti) can be used for the second electric conductors 55. However, other electrically conductive materials may also be used for the second electric conductors 55.

As shown in FIG. 3, within a single driving row 31, the first elements 23 are arranged with equal pitches (=S1). Here, within a single driving row 31, k-th vibration films ("k"=1, 2, ... n) 25a, 25b, 25c ... are specified in increasing order of distance from the second straight line LN2. The first vibration film 25a is disposed at a first distance St from the second straight line LN2. The second vibration film 25b is disposed at a second distance St+S1 from the second straight line LN2, the second distance being larger than the first distance St. The third vibration film 25c is disposed at a third distance St+2×S1 from the second straight line LN2, the third distance being larger than the second distance St+S1.

In this manner, a k-th vibration film 25 is disposed further away from the second straight line LN2 than a (k−1)-th vibration film 25.

Within a single reverberation suppression row 32, k-th vibration films 26 are specified in increasing order of distance from the second straight line LN2. A first vibration film 26a is disposed next to the first vibration film 25a of the driving row 31 at a first propagation distance D1 from that vibration film 25a. A second vibration film 26b is disposed next to the second vibration film 25b of the driving row 31 at a second propagation distance D2 that is larger than the first propagation distance D1 from that vibration film 25b. A third vibration film 26c is disposed next to the third vibration film 25c of the driving row 31 at a third propagation distance D3 that is larger than the second propagation distance D2 from that vibration film 25c. In this manner, when the distance between a first element 23 included in the driving row 31, the first element 23 being the k-th first element ("k" is an integer between 1 and n/2−1 inclusive) in increasing order of distance from the second straight line LN2, and a second element 24 included in the reverberation suppression row 32, the second element 24 being the k-th second element in increasing order of distance from the second straight line LN2, is represented by $D_k$, a relationship $D_k < D_{k+1}$ is satisfied with respect to at least one value of "k". Here, when the distance between two first elements 23 included in the driving row 31, the first elements 23 respectively being the j-th ("j" is an integer between 1 and n/2−1 inclusive) first element and the (j+1)-th first element in increasing order of distance from the second straight line LN2, is represented by $S1_j$, and the distance between two second elements 24 included in the reverberation suppression row 32, the second elements 24 respectively being the j-th second element and the (j+1)-th second element in increasing order of distance from the second straight line LN2, is represented by $S2_j$, relationships $S1_j \leq S1_{j+1}$ and $S2_j \leq S2_{j+1}$ are satisfied. As a result, relationships $S1_j < S2_j$ and $S1_{1+1} < S2_{1+1}$ are satisfied. Moreover, with respect to every value of "k", the relationship $D_k < D_{k+1}$ is satisfied.

A plurality of third electric conductors 57 are formed on the surface of the base 21. The third electric conductors 57 extend in parallel in the column direction of the arrangement. A single third electric conductor 57 is assigned to each column of the first elements 23 and the second elements 24. A single third electric conductor 57 is connected commonly to the piezoelectric films 47 and 54 of the first elements 23 and the second elements 24 that are lined up in the column direction of the arrangement. Each third electric conductor 57 forms the top electrodes 45, 52 for the individual elements 23, 24. The two ends of each third electric conductor 57 are respectively connected to a pair of extraction interconnects 58. The extraction interconnects 58 extend parallel to each other in the row direction of the arrangement. The two ends of each extraction interconnect 58 are connected to the corresponding top electrode terminals 34 and 37, respectively. In this manner, the top electrodes 45 and 52 are connected commonly to the elements 23 and 24 of the entire matrix. The third electric conductors 57 can be formed of, for example, iridium (Ir). However, other electrically conductive materials may also be used for the third electric conductors 57.

Figure 4:
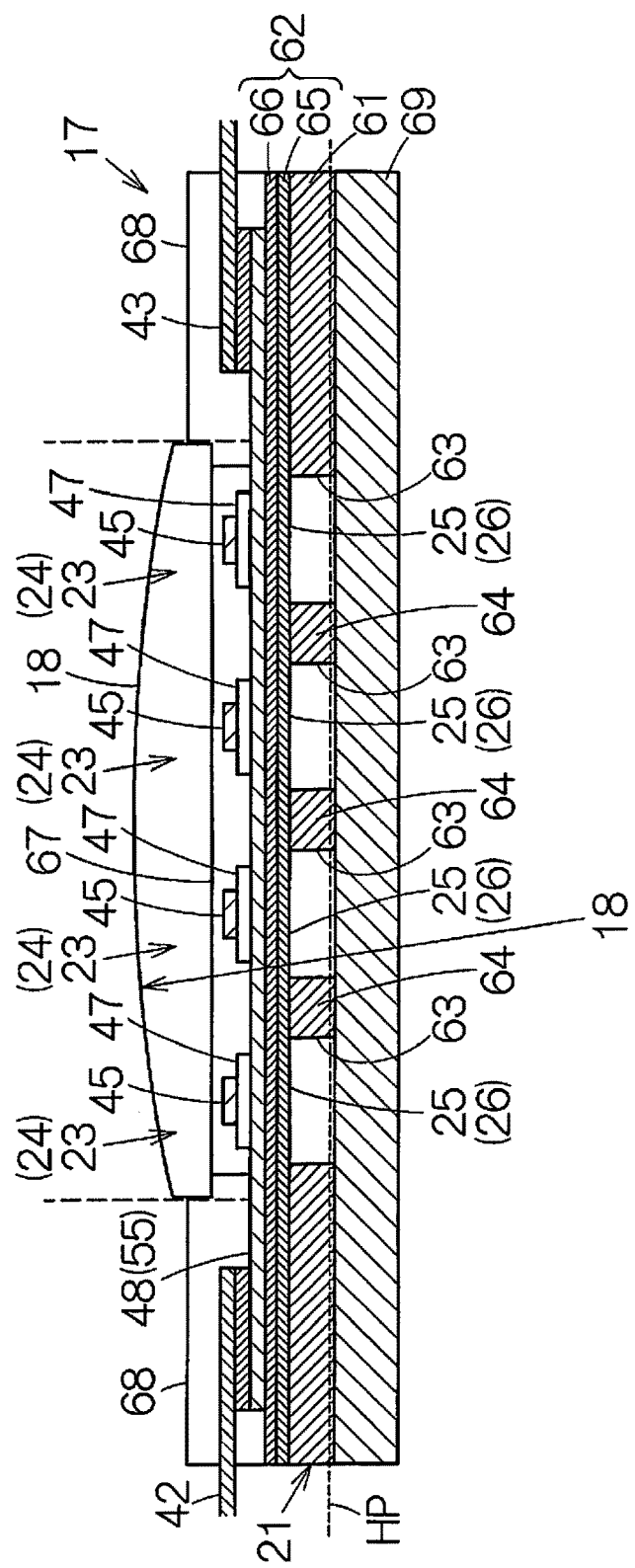
FIG. 4 is a cross-sectional view taken along line A-A in FIG. 1.

As shown in FIG. 4, the base 21 includes a substrate 61 and a coating film 62. The coating film 62 is laminated over the entire surface of the substrate 61. In the substrate 61, an opening 63 is formed for each of the first elements 23 and the second elements 24. The openings 63 define respective spaces that are hollowed out from a back surface of the substrate 61 and that pass through the substrate 61. The openings 63 are arranged in an array in the substrate 61. The outline of a region where the openings 63 are arranged corresponds to the outline of the element array region 27. The substrate 61 can be formed of, for example, a silicon substrate.

A partitioning wall 64 is disposed between every two adjacent openings 63. Adjacent openings 63 are separated from each other by the partitioning walls 64. The wall thickness of the partitioning walls 64 corresponds to the spacing between the openings 63. Each partitioning wall 64 defines two wall surfaces within planes that extend parallel to each other. The wall thickness corresponds to the distance between the two wall surfaces. That is to say, the wall thickness can be defined by the length of a normal line that extends between the wall surfaces orthogonally to the wall surfaces.

The coating film 62 is composed of a silicon oxide ($SiO_2$) layer 65 that is laminated on the surface of the substrate 61 and a zirconium oxide ($ZrO_2$) layer 66 that is laminated on a surface of the silicon oxide layer 65. The coating film 62 is in contact with the openings 63. Thus, portions of the coating film 62 that correspond to the respective outlines of the openings 63 form the vibration films 25, 26. The vibration films 25, 26 refer to those portions of the coating film 62 that face the respective openings 63 and that can thus vibrate in the thickness direction of the substrate 61. The film thickness of the silicon oxide layer 65 can be determined based on resonance frequency.

The bottom electrode 46 (53), the piezoelectric film 47 (54), and the top electrode 45 (52) are sequentially laminated on the surface of each vibration film 25 (26). The piezoelectric film 47 (54) can be formed of, for example, lead zirconate titanate (PZT). Other piezoelectric materials may also be used for the piezoelectric film 47 (54). Here, the piezoelectric film 47 (54) under the third electric conductor 57 completely covers the first electric conductor 48 (or the second electric conductor 55). The piezoelectric films 47 and 54 can serve to avoid short-circuiting of the third electric conductors 57 with the first and second electric conductors 48 and 55.

An acoustic matching layer 67 is laminated over the surface of the base 21. The acoustic matching layer 67 covers the element array 22. The film thickness of the acoustic matching layer 67 is determined in accordance with the resonance frequency of the vibration films 25 and 26. For example, a silicone resin film can be used for the acoustic matching layer 67. The acoustic matching layer 67 fits within a space between the first terminal array 33a and the second terminal array 33b. The edges of the acoustic matching layer 67 are spaced apart from the first side 21a and the second side 21b, respectively, of the base 21. The acoustic matching layer 67 has an outline that is smaller than the outline of the base 21.

The acoustic lens 18 is disposed on the acoustic matching layer 67. The acoustic lens 18 is in close contact with a surface of the acoustic matching layer 67. The acoustic matching layer 67 serves to allow the acoustic lens 18 to adhere to the base 21. The partial cylindrical surface 18a of the acoustic lens 18 has generating lines that are parallel to the third electric conductors 57. The curvature of the partial cylindrical surface 18a is determined in accordance with the focus position of ultrasonic waves emitted from a single row of first elements 23 connected to a single first electric conductor 48. The acoustic lens 18 may be formed of, for example, a silicone resin. The acoustic lens 18 has an acoustic impedance that is similar to the acoustic impedance of a living body.

A protective film 68 is fixed to the base 21. The protective film 68 may be formed of, for example, a material that is impervious to water, such as an epoxy resin. However, the protective film 68 may also be formed of other resin materials. The protective film 68 is fixed to side surfaces of the acoustic lens 18 and the acoustic matching layer 67. The protective film 68 overlaps the first electric conductors 48, the second electric conductors 55, and the extraction interconnects 58 on the surface of the base 21 in regions between the acoustic matching layer 67 and the first and second wiring boards 42, 43. Similarly, the protective film 68 overlaps end portions of the first wiring board 42 and the second wiring board 43 on the base 21.

A backing material 69 is attached to the back surface of the base 21. The back surface of the base 21 is superposed on a surface of the backing material 69. The backing material 69 closes the openings 63 in the back surface of the ultrasonic device 17. The backing material 69 can be provided with a rigid base material. Herein, the partitioning walls 64 are coupled to the backing material 69 at their joint surfaces. The backing material 69 is joined to each partitioning wall 64 in at least one joint region. An adhesive can be used to join the backing material 69 to the partitioning walls 64.

(3) Circuit Configuration of Ultrasonic Diagnostic Apparatus

Figure 5:
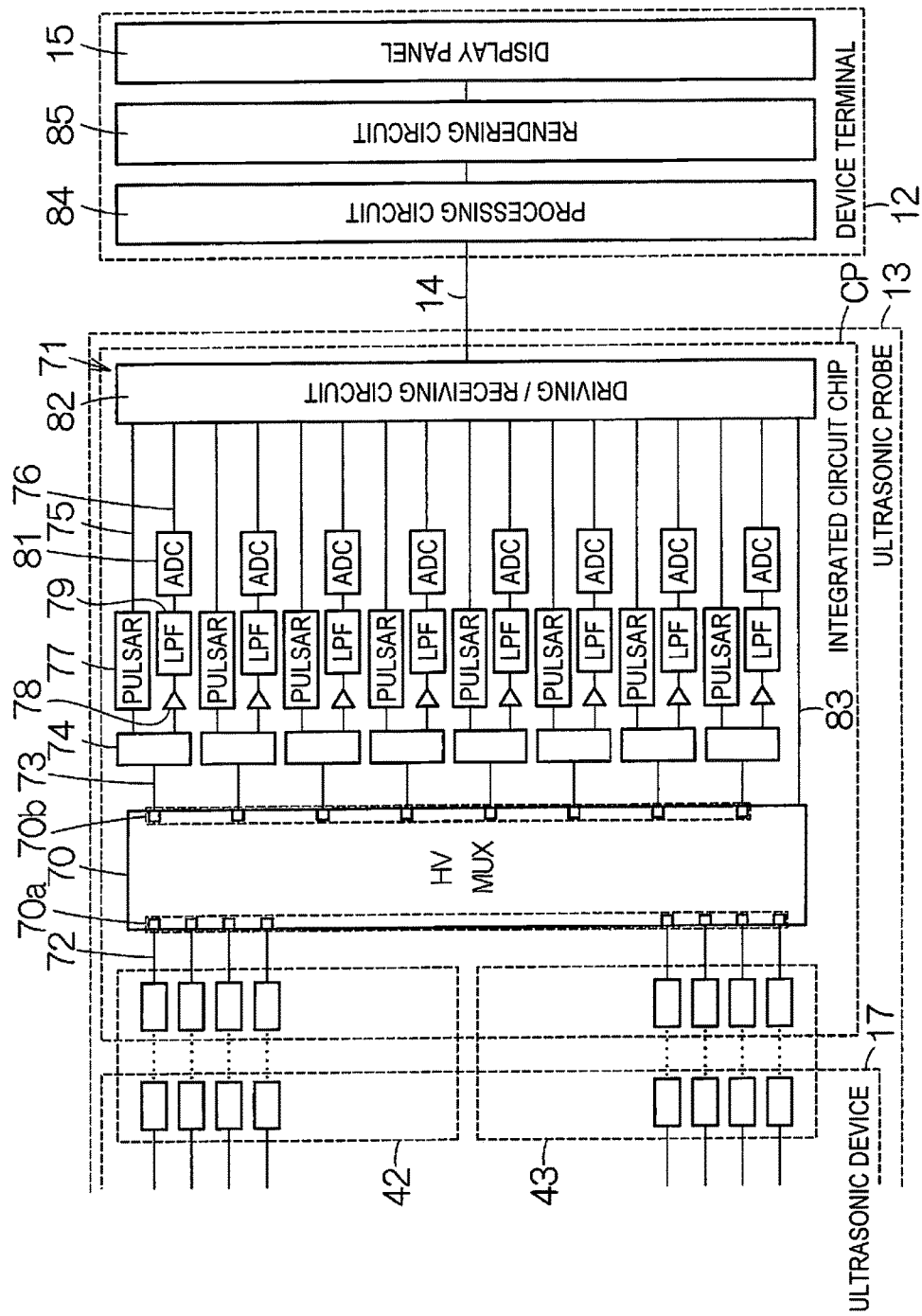
FIG. 5 is a block diagram schematically showing a circuit configuration of the ultrasonic diagnostic apparatus.

As shown in FIG. 5, the ultrasonic diagnostic apparatus 11 is provided with an integrated circuit chip (transmitting unit) CP electrically connected to the ultrasonic device 17. The integrated circuit chip CP is provided with a multiplexer 70 and a transmitting/receiving circuit 71. The multiplexer 70 is provided with a port group 70a on the side of the ultrasonic device 17 and a port group 70b on the side of the transmitting/receiving circuit 71. The first signal lines of the first wiring board 42 and the second signal lines of the second wiring board 43 are connected via wires 72 to the port group 70a on the side of the ultrasonic device 17. The port group 70a is thus connected to the element array 22. Herein, the port group 70b on the side of the transmitting/receiving circuit 71 is connected to a specified number of signal lines 73 within the integrated circuit chip CP. The specified number corresponds to the number of rows of the first elements 23 that are simultaneously driven during scanning. The multiplexer 70 manages mutual connection between the ports on the side of the cable 14 and the ports on the side of the ultrasonic device 17.

The transmitting/receiving circuit 71 is provided with a specified number of switches 74. The individual switches 74 are connected to the corresponding signal lines 73. The transmitting/receiving circuit 71 is provided with a transmitting path 75 and a receiving path 76 for each switch 74. The transmitting paths 75 and the receiving paths 76 are connected to the switches 74 in parallel. Each switch 74 selectively connects the transmitting path 75 or the receiving path 76 to the multiplexer 70. A pulsar (first driving control unit) 77 is incorporated in each of the transmitting paths 75. The pulsar 77 outputs a pulse signal at a frequency corresponding to the resonance frequency of the vibration film 25. An amplifier 78, a low-pass filter (LPF) 79, and an analog-digital converter (ADC) 81 are incorporated in each receiving path 76. Output signals of the first elements 23 are amplified and converted into digital signals.

The integrated circuit chip CP is provided with a driving/receiving circuit 82. The transmitting paths 75 and the receiving paths 76 are connected to the driving/receiving circuit 82. The driving/receiving circuit 82 simultaneously controls the pulsars 77 in accordance with the form of scanning. The driving/receiving circuit 82 receives the digital signals of the output signals in accordance with the form of scanning. The driving/receiving circuit 82 is connected to the multiplexer 70 via a control line 83. The multiplexer 70 manages the mutual connection based on a control signal supplied from the driving/receiving circuit 82.

A processing circuit 84 is incorporated in the device terminal 12. The processing circuit 84 can be provided with a central processing unit (CPU) and a memory, for example. The overall operation of the ultrasonic diagnostic apparatus 11 is controlled in accordance with the processing of the processing circuit 84. The processing circuit 84 controls the driving/receiving circuit 82 in accordance with an instruction input from a user. The processing circuit 84 generates an image according to the output signals of the first elements 23. The image is identified by rendering data.

A rendering circuit 85 is incorporated in the device terminal 12. The rendering circuit 85 is connected to the processing circuit 84. The display panel 15 is connected to the rendering circuit 85. The rendering circuit 85 generates a driving signal according to the rendering data generated in the processing circuit 84. The driving signal is fed to the display panel 15. As a result, an image is shown on the display panel 15.

(4) Operation of Ultrasonic Diagnostic Apparatus

Next, the operation of the ultrasonic diagnostic apparatus 11 will be briefly described. To transmit ultrasonic waves, a pulse signal is supplied to the piezoelectric elements 44 of the first elements 23. The pulse signal is supplied to the first elements 23 on a row-by-row basis through the bottom electrode terminals 35 and 38 and the top electrode terminals 34 and 37. In each of the first elements 23, an electric field acts on the piezoelectric film 47 between the bottom electrode 46 and the top electrode 45. The piezoelectric film 47 vibrates at the frequency of ultrasonic waves. The vibration of the piezoelectric film 47 is transferred to the vibration film 25. Thus, the vibration film 25 vibrates ultrasonically. As a result, a desired ultrasonic beam is emitted toward the subject (for example, the interior of a human body).

Reflected waves of the ultrasonic waves vibrate the vibration film 25 of the first element 23. The ultrasonic vibration of the vibration film 25 ultrasonically vibrates the piezoelectric film 47 at a desired frequency. A voltage is output from the piezoelectric element 44 in accordance with the piezoelectric effect of the piezoelectric element 44. In each of the first elements 23, a potential is generated between the top electrode 45 and the bottom electrode 46. The generated potentials are output from the bottom electrode terminals 35 and 38 and the top electrode terminals 34 and 37 as electric signals. The ultrasonic waves are detected in this manner.

Ultrasonic waves are repeatedly transmitted and received. As a result, a linear scan or a sector scan is achieved. When the scan is completed, an image is formed based on digital signals of the output signals. The image thus formed is displayed on the screen of the display panel 15.

While a pulse signal is supplied to the piezoelectric elements 44 of a driving row 31, a pulse signal is supplied to the piezoelectric elements 51 of a reverberation suppression row 32 adjacent thereto. The pulse signal is supplied to the second elements 24 on a row-by-row basis via the bottom electrode terminals 35 and 38 and the top electrode terminals 34 and 37. In each second element 24, an electric field acts on the piezoelectric film 54 between the bottom electrode 53 and the top electrode 52. The piezoelectric film 54 vibrates at the frequency of ultrasonic waves. The vibration of the piezoelectric film 54 is transferred to the vibration film 26. Thus, the vibration film 26 vibrates ultrasonically. Ultrasonic vibration of a k-th vibration film 26 in increasing order of distance from the second straight line LN2 propagates through the acoustic matching layer 67 and is transmitted to the vibration film 25 of a corresponding k-th first element 23. Reverberant vibration of the vibration films 25a, 25b, . . . of a driving row 31 is at least partially cancelled out in accordance with the propagation of ultrasonic vibration of the vibration films 26a, 26b, . . . of a corresponding reverberation suppression row 32.

The inventor of the invention newly found a certain fact. According to that fact, it was found that in the ultrasonic device 17, the nearer the centroid 28 (second straight line LN2) of the element array region 27, the shorter the cycle of reverberant vibration. Therefore, when the vibration films 25a, 25b, . . . of a driving row 31 generate vibration at the same time, the phase of reverberant vibration of a (k+1)-th vibration film 25b, 25c, . . . lags behind that of a k-th vibration film 25a, 25b, . . . , which is nearer to the second straight line LN2. When the vibration films 26a, 26b, . . . of an adjacent reverberation suppression row 32 generate vibration at the same time, the vibration that propagates from the vibration films 26a, 26b, . . . reaches corresponding k-th vibration films 25a, 25b, . . . with time lags according to the propagation distances D1, D2, . . . Dn. Thus, the vibration films 26a, 26b, . . . of the reverberation suppression row 32 can serve to reduce reverberant vibration of the vibration films 25a, 25b, . . . of the driving row 31.

In the ultrasonic device 17, when the distance between two first elements 23 included in a driving row 31, the first elements 23 respectively being the j-th ("j" is an integer between 1 and n/2−1 inclusive) first element and the (j+1)-th first element in increasing order of distance from the second straight line LN2, is represented by $S1_j$, and the distance between two second elements 24 included in a reverberation suppression row 32, the second elements 24 respectively being the j-th second element and the (j+1)-th second element in increasing order of distance from the second straight line LN2, is represented by $S2_j$, the relationships $S1_j \leq S1_{j+1}$ and $S2_j \leq S2_{j+1}$ are satisfied. Those elements 23, 24 that belong to the same element row 31, 32 are driven by the same driving signal. Since the relationship $S1_j \leq S1_{j+1}$ and the relationship $S2_j \leq S2_{j+1}$ are established within the same element row, vibration propagating between the j-th elements 23 and 24 and between the (j+1)-th elements 23 and 24 according to the distance from the second straight line LN2 can synchronize with vibration of the destinations of propagation. Thus, propagation contributes to a reduction of residual vibration.

In the ultrasonic device 17, the second elements 24 included in a reverberation suppression row 32 are arranged along a straight line that is parallel to the first straight line LN1, and $S1_j$, $S1_{j+1}$, $S2_j$, and $S2_{j+1}$ satisfy the relationships $S1_j < S2_j$ and $S1_{j+1} < S2_{j+1}$. At this time, the arrangement of the reverberation suppression rows 32 extends parallel to the arrangement of the driving rows 31. Accordingly, the distance between the element rows 31 and 32 along the second straight line LN2 can be reduced as far as possible, that is, minimized. Thus, the elements 23 and 24 can be efficiently arranged.

In the ultrasonic device 17, the distance $D_k$ satisfies the relationship $D_k < D_{k+1}$ with respect to every value of "k". Synchronization of vibration between the elements 23 and 24 is secured. Residual vibration can thus be reliably reduced.

Here, the area of the vibration film 25 of each first element 23 included in the driving rows 31 is larger than the area of the vibration film 26 of each second element 24 included in the reverberation suppression rows 32. During formation of an ultrasonic beam, vibration of the second elements 24 included in the reverberation suppression rows 32 is not transmitted to the outside from the acoustic matching layer 67 and mainly helps to reduce reverberant vibration. Vibration control can thus be simplified.

(5) Structure of Ultrasonic Device According to Second Embodiment

Figure 6:
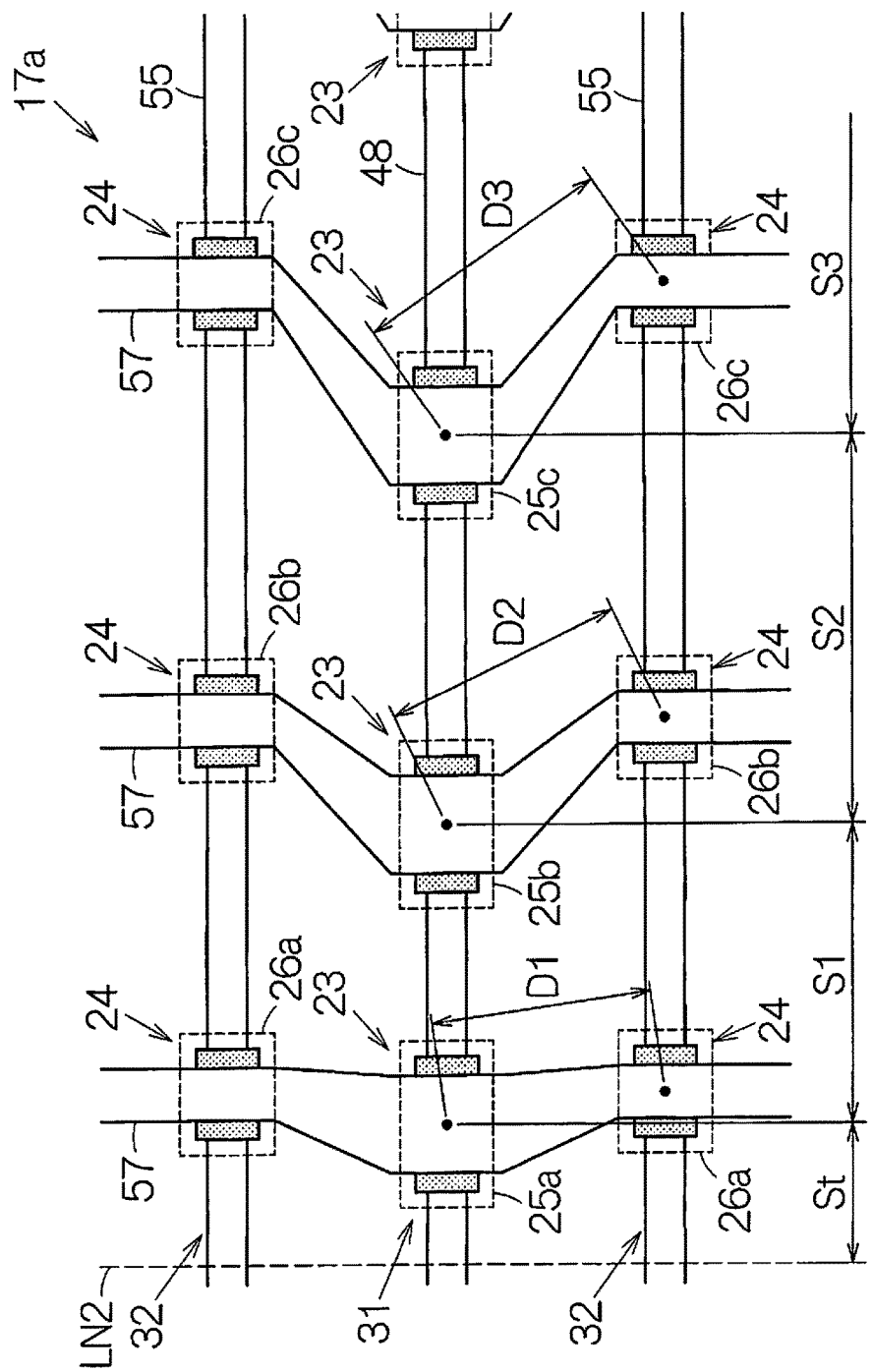
FIG. 6 is a partial enlarged plan view of an ultrasonic device according to a second embodiment.

FIG. 6 shows an enlarged partial plan view of an ultrasonic device 17a according to a second embodiment. In the ultrasonic device 17a, when k-th vibration films ("k"=1, 2, ... n) 25a, 25b, ... are specified in increasing order of distance from the second straight line LN2 within a single driving row 31, the distance between a k-th vibration film 25 and a (k+1)-th vibration film 25 is smaller than the distance between the (k+1)-th vibration film 25 and a (k+2)-th vibration film 25. For example, the distance S1 between the k-th vibration film 25a and the (k+1)-th vibration film 25b is smaller than the distance S2 between the (k+1)-th vibration film 25b and the (k+2)-th vibration film 25c. Also, the distance S2 between the (k+2)-th vibration film 25b and a (k+3)-th vibration film 25c is smaller than the distance S3 between the (k+3)-th vibration film 25c and a (k+4)-th vibration film 25. Here, the vibration films 25a, 25b, ... of the first elements 23 are arranged in a single straight line. Since the vibration films 25a, 25b, ... in each driving row 31 are arranged in a single straight line in this manner, the first electric conductors 48 can be formed linearly. The first electric conductors 48 can thus be easily formed. Moreover, the vibration films 25a, 25b, ... of the driving rows 31 can be efficiently arranged.

Figure 7:
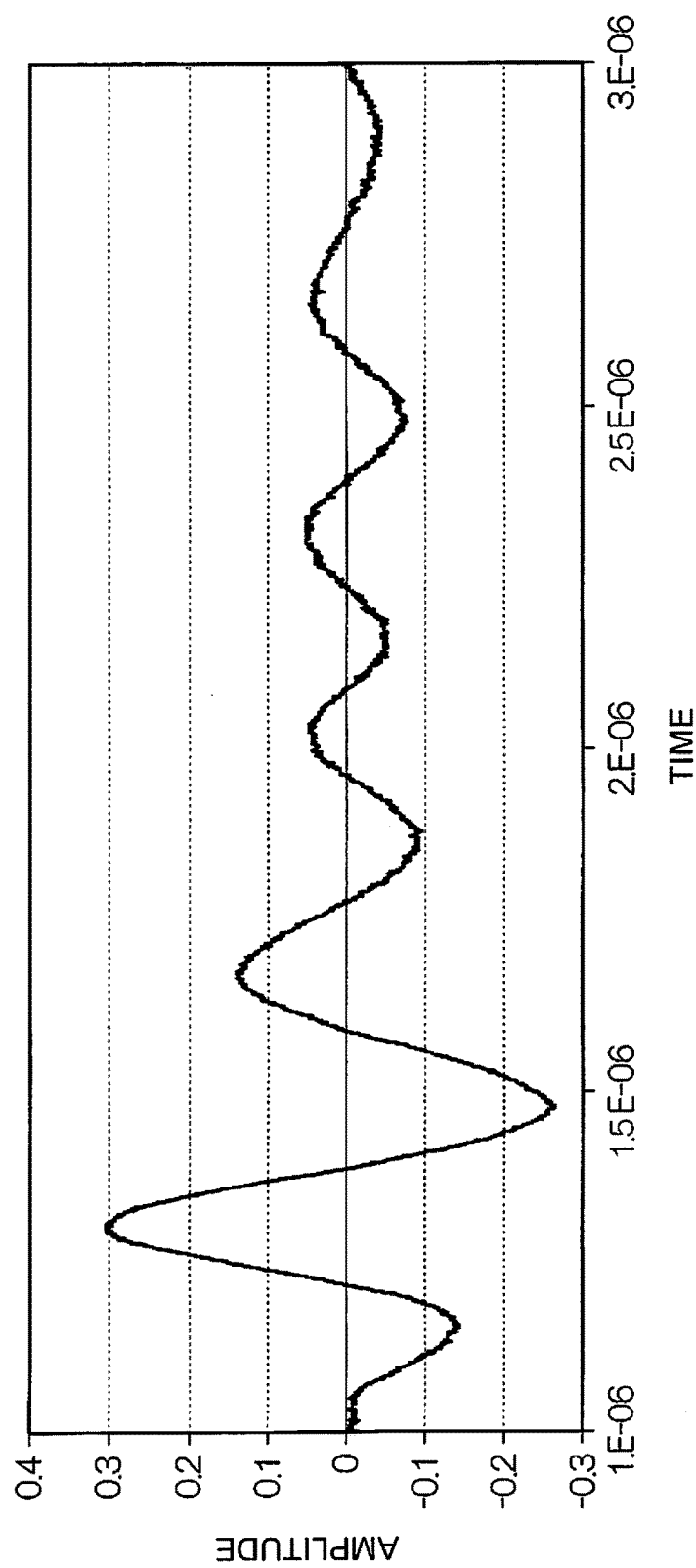
FIG. 7 is a graph showing reverberant vibration of a first ultrasonic transducer element.
Figure 8:
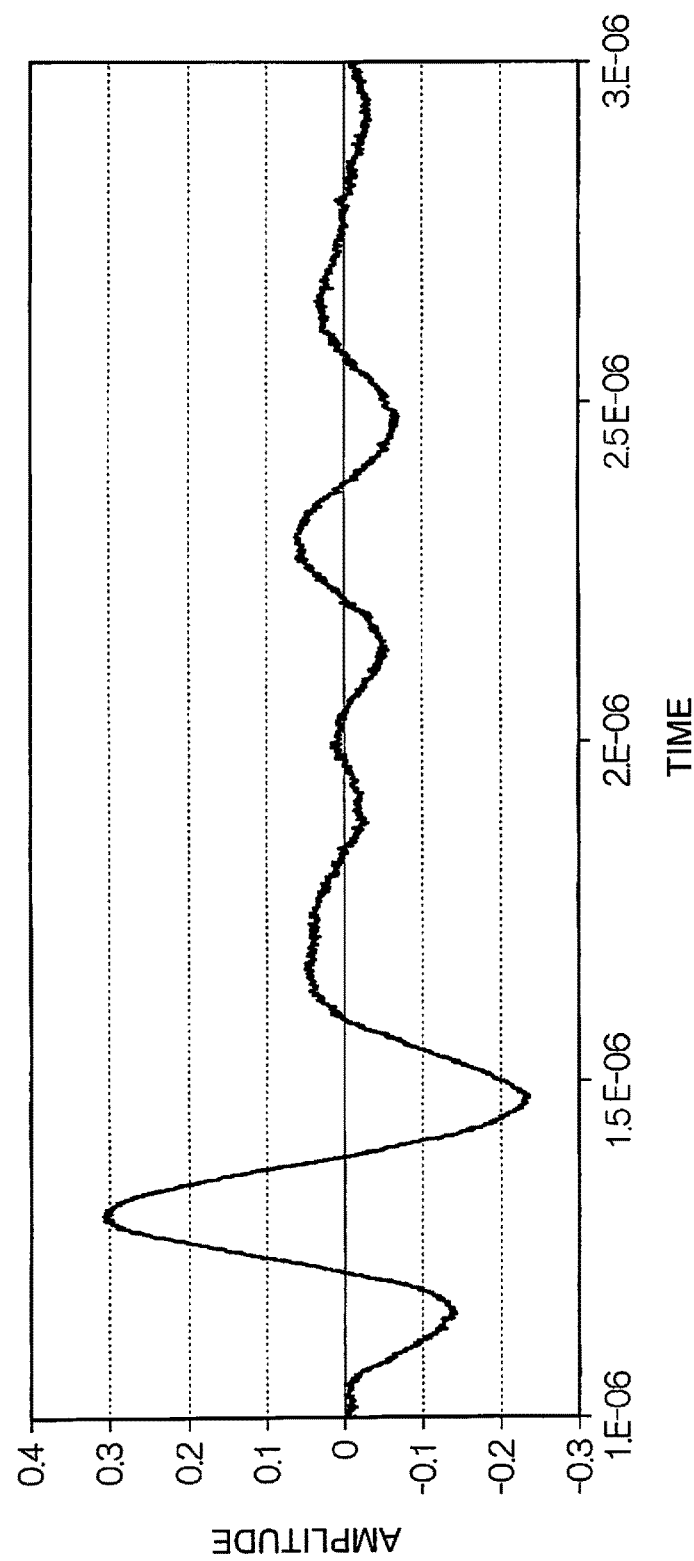
FIG. 8 is a graph showing reverberant vibration of the first ultrasonic transducer element when a second ultrasonic transducer element ultrasonically vibrates at the same time.

The inventor of the invention examined reverberant vibration of the first elements 23 based on the second embodiment. A pulse signal was supplied to the first elements 23 of a driving row 31. Ultrasonic vibration of the first elements 23 was simultaneously induced in response to the supply of the pulse signal. In one first element 23, for example, as shown in FIG. 7, generation of reverberant vibration was observed by the action of transverse propagation through the acoustic matching layer 67. Next, a pulse signal was supplied to the first elements 23 of the driving row 31, and at the same time, a pulse signal was supplied to the second elements 24 of a reverberation suppression row 32. Ultrasonic vibration of the first elements 23 was induced in the same manner as described above, and at the same time, ultrasonic vibration of the second elements 24 was induced. In accordance with the propagation distance between a second element 24 of the reverberation suppression row 32 and a corresponding first element 23 of the driving row 31, ultrasonic vibration having a phase opposite to that of reverberant vibration of the first element 23 was generated in the second element 24. As a result, as shown in FIG. 8, a reduction of residual vibration was observed.

Figure 9:
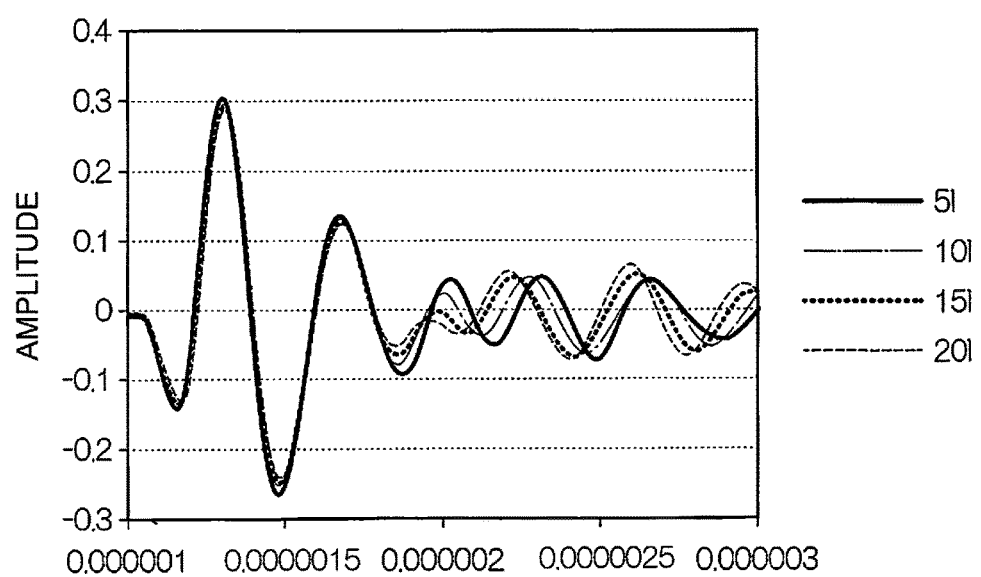
FIG. 9 is graph showing reverberant vibration of the first ultrasonic transducer element plotted as a function of distance from a neutral axis.

The inventor of the invention newly found a certain fact. The inventor of the invention examined residual vibration of a single row of first elements 23. A pulse signal was supplied to the first elements 23 of a driving row 31. Ultrasonic vibration of the first elements 23 was simultaneously induced in response to the supply of the pulse signal. As a result, as shown in FIG. 9, generation of reverberant vibration was observed. When a plurality of vibration films vibrate simultaneously, the vibration of each vibration film propagates through, for example, the acoustic matching layer to an adjacent vibration film. So-called crosstalk was induced. As is clear from FIG. 9, the nearer the centroid 28 (second straight line LN2) of the element array region 27, the shorter the cycle of reverberant vibration.

(6) Structure of Ultrasonic Device According to Third Embodiment

Figure 10:
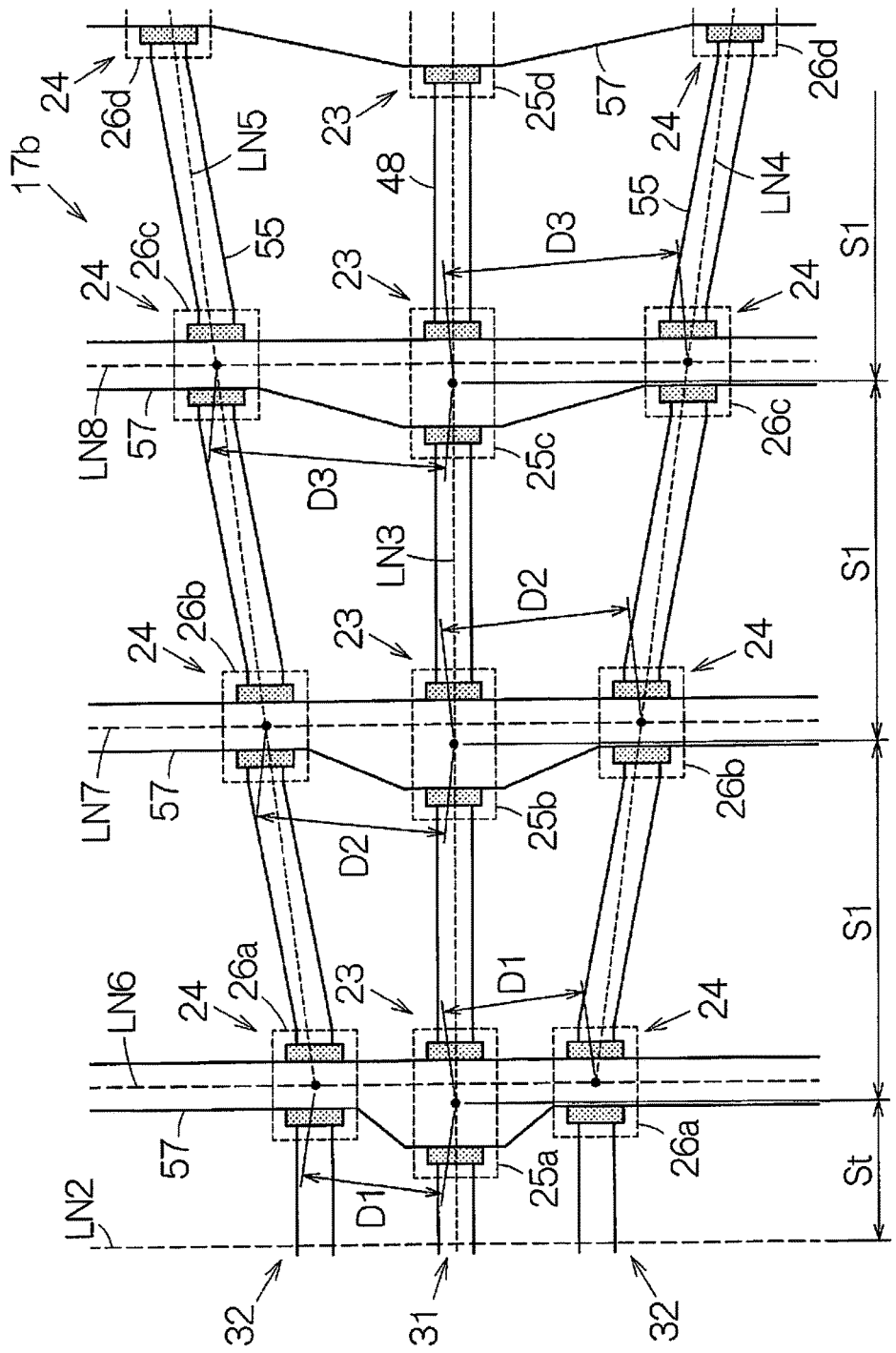
FIG. 10 is a partial enlarged plan view of an ultrasonic device according to a third embodiment.

FIG. 10 is an enlarged partial plan view of an ultrasonic device 17b according to a third embodiment. In the ultrasonic device 17b, two reverberation suppression rows 32 on both sides of a single driving row 31 are assigned to that driving row 31. The vibration films 25 of a group of first elements 23 belonging to the driving row 31 are arranged in a third straight line LN3 in the row direction of the arrangement. The vibration films 26 of a group of second elements 24 belonging to one of the reverberation suppression rows 32 are arranged in a fourth straight line LN4 in the row direction of the arrangement. The vibration films 26 of a group of second elements 24 belonging to the other reverberation suppression row 32 are arranged in a fifth straight line LN5 in the row direction of the arrangement. The distance between the third straight line LN3 and the fourth straight line LN4 and the distance between the third straight line LN3 and the fifth straight line LN5 increase with the distance from the centroid 28 (second straight line LN2). That is to say, the second elements 24 included in the reverberation suppression rows 32 are disposed along the two line-symmetrical straight lines LN4 and LN5, where the third straight line LN3 is the axis of symmetry.

The third electric conductors 57 extend parallel to one another in the column direction of the arrangement. A k-th vibration film 25a belonging to the driving row 31 and k-th vibration films 26a belonging to the respective reverberation suppression rows 32 are arranged in a common straight line LN6. Similarly, a (k+1)-th vibration film 25b belonging to the driving row 31 and (k+1)-th vibration films 26b belonging to the reverberation suppression rows 32 are arranged in a common single straight line LN7, and a (k+2)-th vibration film 25c belonging to the driving row 31 and (k+2)-th vibration films 26c belonging to the reverberation suppression rows 32 are arranged in a common single straight line LN8. Here, the vibration film 26a in the fourth straight line LN4 is disposed next to the first vibration film 25a of the driving row 31 while being spaced apart therefrom by a first propagation distance D1, whereas the vibration film 26a in the fifth straight line LN5 is disposed on a side opposite to the former vibration film 26a so as to be next to the vibration film 25a while being spaced apart therefrom by the first propagation distance D1. Similarly, the second vibration film 26b in the fourth straight line LN4 is disposed next to the second vibration film 25b while being spaced apart therefrom by a second propagation distance D2, whereas the vibration film 26b in the fifth straight line LN5 is disposed on a side opposite to the former vibration film 26b so as to be next to the second vibration film 25b while being spaced apart therefrom by the second propagation distance D2. In this manner, while the third electric conductors 57 are formed linearly, a k-th vibration film 26 is disposed next to a corresponding vibration film 25 while being spaced apart therefrom by a distance that is larger than the distance by which a (k−1)-th vibration film 26 is spaced apart from its corresponding vibration film 25.

In the ultrasonic device 17b, the third electric conductors 57 can be commonly formed in the column direction of the arrangement so as to extend across the driving rows 31 and the reverberation suppression rows 32. Since the vibration films 25 and the vibration films 26 of the driving rows 31 and the reverberation suppression rows 32 are arranged in straight lines, the common third electric conductors 57 can be formed linearly. Thus, the third electric conductors 57 can be easily formed. In this manner, while the third electric conductors 57 are formed linearly, the first propagation distance D1 is secured between each of the k-th vibration films 26 and the k-th vibration film 25, and the second propagation distance D2 is secured between each of the (k+1)-th vibration films 26 and the (k+1)-th vibration film 25.

In the ultrasonic device 17b, the reverberation suppression rows 32 are formed by not only the second elements 24 that are arranged along the fourth straight line LN4, but also the second elements 24 that are arranged along the fifth straight line LN5. At this time, when the distance between a first element 23 included in the driving row 31, the first element 23 being the k-th first element ("k" is an integer between 1 and n/2−1 inclusive) in increasing order of distance from the second straight line LN2, and a second element 24 included in the reverberation suppression row 32 extending in the fifth straight line LN5, the second element being the k-th second element in increasing order of distance from the second straight line LN2, is represented by $D2_k$, a relationship $D2_k < D2_{k+1}$ is satisfied with respect to at least one value of "k". Thus, a single channel can be formed by three element rows.

In this ultrasonic device 17b, the second elements 24 included in each reverberation suppression row 32 are arranged along two line-symmetrical straight lines, where the second straight line LN2 is the axis of symmetry. At this time, when the distance L1*i* from the second straight line LN2 to a first element 23 included in the driving row 31, the first element 23 being the i-th ("i" is an integer between 1 and n/2 inclusive) first element in increasing order of distance from the second straight line LN2, is equal to the distance L2*i* from the second straight line LN2 to a second element 24 included in the reverberation suppression row 32, the second element 24 being the i-th second element in increasing order of distance from the second straight line LN2. Thus, the arrangements in odd rows are disposed parallel to one another, and the arrangements in even rows are disposed parallel to one another.

Figure 11:
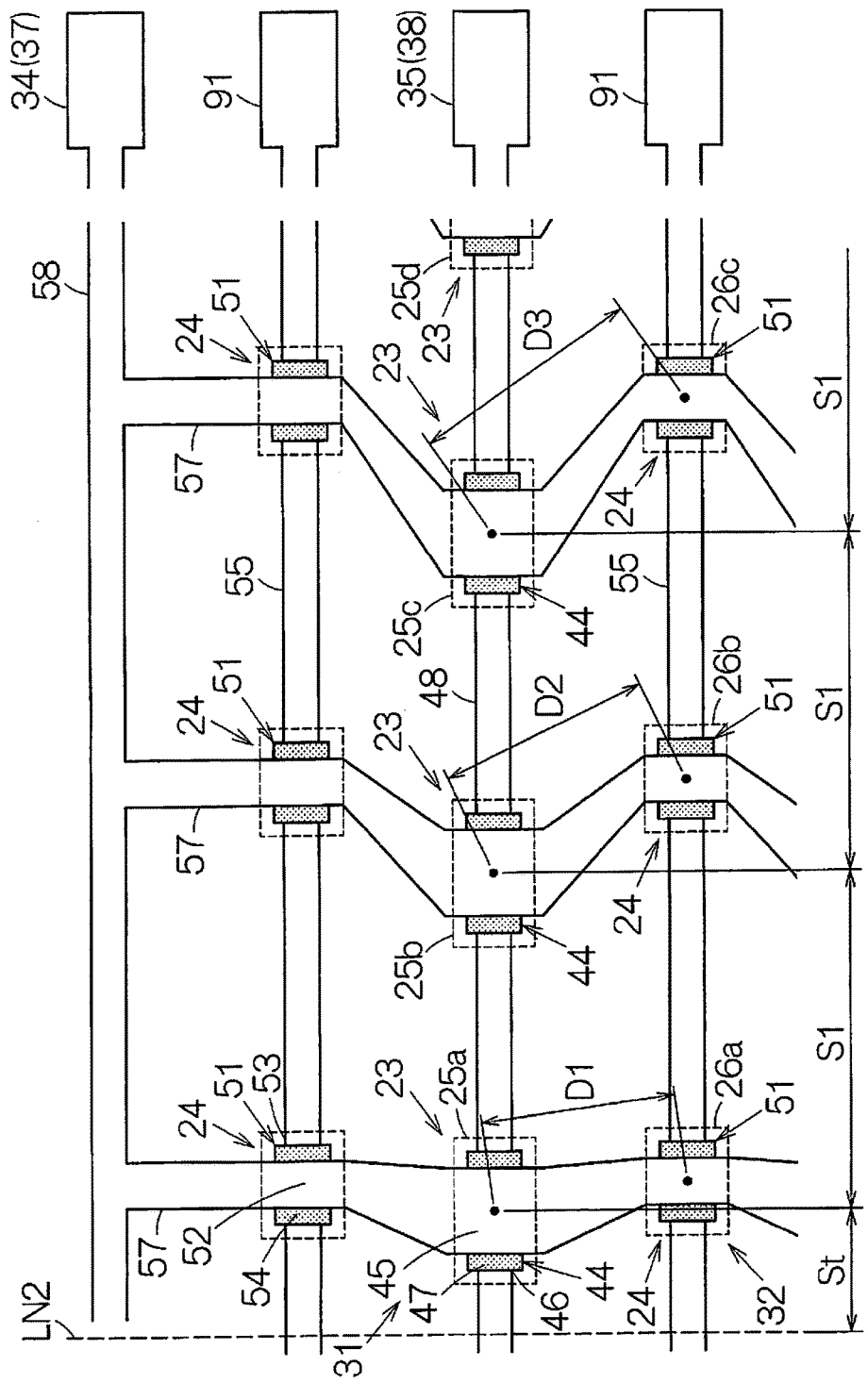
FIG. 11 is a partial enlarged plan view corresponding to FIG. 3 and showing an ultrasonic device according to a modification.

In the above-described ultrasonic devices 17, 17a, and 17b, when "n" is an odd number, a first element 23 and a second element 24 at a distance=0 from the second straight line LN2 are present. Moreover, further ultrasonic transducer elements may also be disposed outside the "n" elements 23, 24. In addition, for example, as shown in FIG. 11, for each reverberation suppression row 32, bottom electrode terminals 91 may also be formed in the first terminal array 33a and the second terminal array 33b. Such bottom electrode terminals 91 can be connected to the second electric conductor 55 for each reverberation suppression row 32. Groups of the second elements 24 of the respective reverberation suppression rows 32 are connected to the multiplexer 70 of the integrated circuit chip CP on a row-by-row basis. The multiplexer 70 can supply a driving signal to each set of the driving rows 31 and the reverberation suppression rows 32 at the same timing.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the device terminal 12, the ultrasonic probe 13, the housing 16, the display panel 15, and the like are not limited to those described in the foregoing embodiments, but may be modified in various manners.

The entire disclosure of Japanese Patent Application No. 2014-156707 filed on Jul. 31, 2014 is expressly incorporated by reference herein.

What is claimed is:

1. An ultrasonic device, comprising:
a first interconnect and a second interconnect that are connected to a first terminal;
a first element row in which "n" ultrasonic transducer elements, "n" being an integer of 4 or more, are arranged at line-symmetrical positions along a first straight line, where a second straight line orthogonal to the first straight line is an axis of symmetry, and are connected to the first interconnect; and
a second element row in which "n" ultrasonic transducer elements are arranged at line-symmetrical positions adjacent to the first element row, where the second straight line is the axis of symmetry, and are connected to the second interconnect,
wherein when a distance between an element included in the first element row, the element being the k-th element in increasing order of distance from the second straight line, "k" being an integer between 1 and n/2−1 inclusive, and an element included in the second element row, the element being the k-th element in increasing order of distance from the second straight line, is represented by $D_k$, a relationship $D_k < D_{k+1}$ is satisfied with respect to at least one value of "k".

2. The ultrasonic device according to claim 1,
wherein when a distance between two elements included in the first element row, the elements respectively being the j-th element and the (j+1)-th element in increasing order of distance from the second straight line, "j" being an integer between 1 and n/2−1 inclusive, is represented by $S1_j$, and a distance between two elements included in the second element row, the elements being the j-th element and the (j+1)-th element in increasing order of distance from the second straight line, is represented by $S2_j$, relationships $S1_j \leq S1_{j+1}$ and $S2_j \leq S2_{j+1}$ are satisfied.

3. The ultrasonic device according to claim 2,
wherein the ultrasonic transducer elements included in the second element row are arranged along a straight line that is parallel to the first straight line, and the distances $S1_j$, $S1_{j+1}$, $S2_j$, and $S2_{j+1}$ satisfy relationships $S1_j < S2_j$ and $S1_{j+1} < S2_{j+1}$.

4. The ultrasonic device according to claim 3,
wherein the distance $D_k$ satisfies the relationship $D_k < D_{k+1}$ with respect to every value of "k".

5. An ultrasonic device, comprising:
a first interconnect and a second interconnect;
a transmitting unit that transmits a driving signal to the first interconnect and the second interconnect at the same timing;
a first element row in which "n" ultrasonic transducer elements, "n" being an integer of 4 or more, are arranged at line-symmetrical positions along a first straight line, where a second straight line orthogonal to the first straight line is an axis of symmetry, and are connected to the first interconnect; and
a second element row in which "n" ultrasonic transducer elements are arranged at line-symmetrical positions adjacent to the first element row, where the second straight line is the axis of symmetry, and are connected to the second interconnect,
wherein when a distance between an element included in the first element row, the element being the k-th element in increasing order of distance from the second straight line, "k" being an integer between 1 and n/2−1 inclusive, and an element included in the second element row, the element being the k-th element in increasing order of distance from the second straight line, is represented by $D_k$, a relationship $D_k < D_{k+1}$ is satisfied with respect to at least one value of "k".

6. The ultrasonic device according to claim 1,
wherein the ultrasonic transducer elements each include a vibration film provided on a base and a driving element provided on the vibration film.

7. The ultrasonic device according to claim 6,
wherein the driving element includes a piezoelectric body and two electrodes provided on the piezoelectric body.

8. The ultrasonic device according to claim 1, further comprising an acoustic matching layer that covers the first element row and the second element row.

9. The ultrasonic device according to claim 6,
wherein an area of each of the vibration films of the ultrasonic transducer elements included in the first element row is larger than an area of each of the vibration films of the ultrasonic transducer elements included in the second element row.

10. The ultrasonic device according to claim 1, comprising:
a third interconnect connected to the first terminal; and
a third element row in which "n" ultrasonic transducer elements are arranged at line-symmetrical positions adjacent to the first element row, where the second straight line is the axis of symmetry, and are connected to the third interconnect,
wherein when a distance between an element included in the first element row, the element being the k-th element in increasing order of distance from the second straight line, "k" being an integer between 1 and n/2−1 inclusive, and an element included in the third element row, the element being the k-th element in increasing order of distance from the second straight line, is represented by $D2_k$, a relationship $D2_k < D2_{k-1}$ is satisfied with respect to the at least one value of "k".

11. The ultrasonic device according to claim 1,
wherein the ultrasonic transducer elements included in the second element row are arranged along two line-symmetrical straight lines, where the second straight line is the axis of symmetry, and
a distance $L1i$ from the second straight line to an element included in the first element row, the element being the i-th element in increasing order of distance from the second straight line, "i" being an integer between 1 and n/2 inclusive, is equal to a distance $L2i$ from the second straight line to an element included in the second element row, the element being the i-th element in increasing order of distance from the second straight line.

12. A probe, comprising:
the ultrasonic device according to claim 1; and
a housing that supports the ultrasonic device.

13. An electronic apparatus, comprising:
the ultrasonic device according to claim 1; and
a processor that is connected to the ultrasonic device and that processes an output from the ultrasonic device.

14. An ultrasonic imaging apparatus, comprising:
the ultrasonic device according to claim 1; and
a display device that displays an image generated based on an output from the ultrasonic device.

15. An ultrasonic device, comprising:
a first element row in which first ultrasonic transducer elements are arranged in a first direction at first intervals, and the same driving signal is input to first ultrasonic transducer elements; and
a second element row in which second ultrasonic transducer elements are arranged in the first direction at second intervals, the same driving signal is input to the second ultrasonic transducer elements,
wherein the first element row and the second element row are arranged line-symmetrically with respect to a center line extending in a second direction that is orthogonal to the first direction, and
the second intervals are larger than the first intervals.

* * * * *